US00PP23265P2

(12) United States Plant Patent
Lemberger

(10) Patent No.: US PP23,265 P2
(45) Date of Patent: Dec. 18, 2012

(54) ***PHLOX PANICULATA* PLANT NAMED 'SHOCKWAVE'**

(50) Latin Name: *Phlox paniculata*
Varietal Denomination: Shockwave

(75) Inventor: Lonette A. Lemberger, Holland, MI (US)

(73) Assignee: Walers Gardens Inc, Zeeland, MI (US)

( * ) Notice: Subject to any disclaimer, the term of this patent is extended or adjusted under 35 U.S.C. 154(b) by 97 days.

(21) Appl. No.: 13/135,678

(22) Filed: Jul. 12, 2011

(51) Int. Cl.
*A01H 5/00* (2006.01)

(52) U.S. Cl. ..... Plt./320

(58) Field of Classification Search ..... Plt./320
See application file for complete search history.

*Primary Examiner* — Howard Locker

(57) ABSTRACT

A new and unique cultivar of Tall Garden *Phlox* named *Phlox paniculata* 'Shockwave' that has variegated leaf margins emerging bright chartreuse and lightening to a creamy yellow and green center, foliage highly resistant to powdery mildew and floriferous stems of about 30 to 45 cm tall producing sweetly-fragrant lavender-pink flowers with white center and lavender-pink eye zones especially suitable as a potted plant, for the garden, for attracting hummingbirds and butterflies, and for cut flower arrangements.

1 Drawing Sheet

Botanical classification: *Phlox paniculata.*
Variety denomination: 'Shockwave'.

BACKGROUND OF THE INVENTION

The present invention relates to a new and distinct cultivar of *Phlox paniculata* plant, known as *Phlox paniculata* 'Shockwave' and will be referred to hereafter by its cultivar name, 'Shockwave', or the "new plant". The new plant was discovered in spring of 2008 and separated out for further evaluation in the summer of 2008 by Lonette A. Lemberger from a tissue-cultured batch greenhouse grown plantlets at a nursery in Zeeland, Mich., USA. The single whole plant mutation originated as an uninduced sport from *Phlox* 'David's Lavender' (not patented). The plant has been asexually propagated by stem cuttings at the same nursery in the greenhouses in Zeeland, Mich. The unique characteristics of the new plant have been found to be reproducible and stable in successive generations of asexually propagated and the resultant plants have been found to be identical to the original selection.

BRIEF SUMMARY OF THE PLANT

*Phlox paniculata* 'Shockwave' is unique from all other Tall Garden *Phlox* known to the inventor. There are several *phlox* with variegated margins including: 'Becky Towe' U.S. Plant Pat. No. 12,908, 'Goldmine' U.S. Plant Pat. No. 12,070, 'Rubymine' U.S. Plant Pat. No. 12,824, 'Silvermine' U.S. Plant Pat. No. 12,764, 'Nihon Kaki' U.S. Plant Pat. No. 12,002, 'Harlequin' (not patented), 'Nora Leigh' (not patented) and 'Triple Play' U.S. Plant Pat. No. 21,329. All of the above listed *Phlox* are from the species *paniculata*_except 'Triple Play' which is a selection from *Phlox glaberrima* ssp. *triflora.*

In addition to having a leaf margin that becomes creamy yellow, 'Shockwave' differs from 'David's Lavender' in being more compact and shorter, the new plant being about half the height.

VARIEGATED PHLOX COMPARISON

| CULTIVAR | VARIEGATION | FLOWER COLOR |
|---|---|---|
| 'Becky Towe' | margin gold becoming creamy | salmon-carmine rose |
| 'David's Lavender' | none | lavender-pink |
| 'Goldmine' | margin chartreuse becoming creamy yellow | bright purple |
| 'Harlequin' | margin creamy white becoming white | fuchsia |
| 'Nihon Kaki' | margin creamy becoming creamy white with random green spots | pink |
| 'Nora Leigh' | margin creamy becoming near white | white with pink eye |
| 'Rubymine' | margin creamy white becoming white | pinkish lavender |
| 'Shockwave' | margin chartreuse becoming creamy yellow | lavender-pink |
| 'Silvermine' | margin golden | white |
| 'Triple Play' | margin creamy white flushed with pink | lavender-pink |

'Shockwave' differs from these listed, the parent sport 'David's Lavender' and all other Tall Garden *Phlox* known to the inventor in the following repeatedly observed traits in combination:

1. Variegated leaf margins emerging bright chartreuse and lightening to a creamy yellow and green center.
2. Foliage highly resistant to powdery mildew.
3. Floriferous stems of about 30 to 45 cm tall producing sweetly-fragrant lavender-pink flowers with white center and lavender-pink eye zones.

BRIEF DESCRIPTION OF THE DRAWINGS

The photographs of the new plant demonstrate the unique traits of 'Shockwave' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
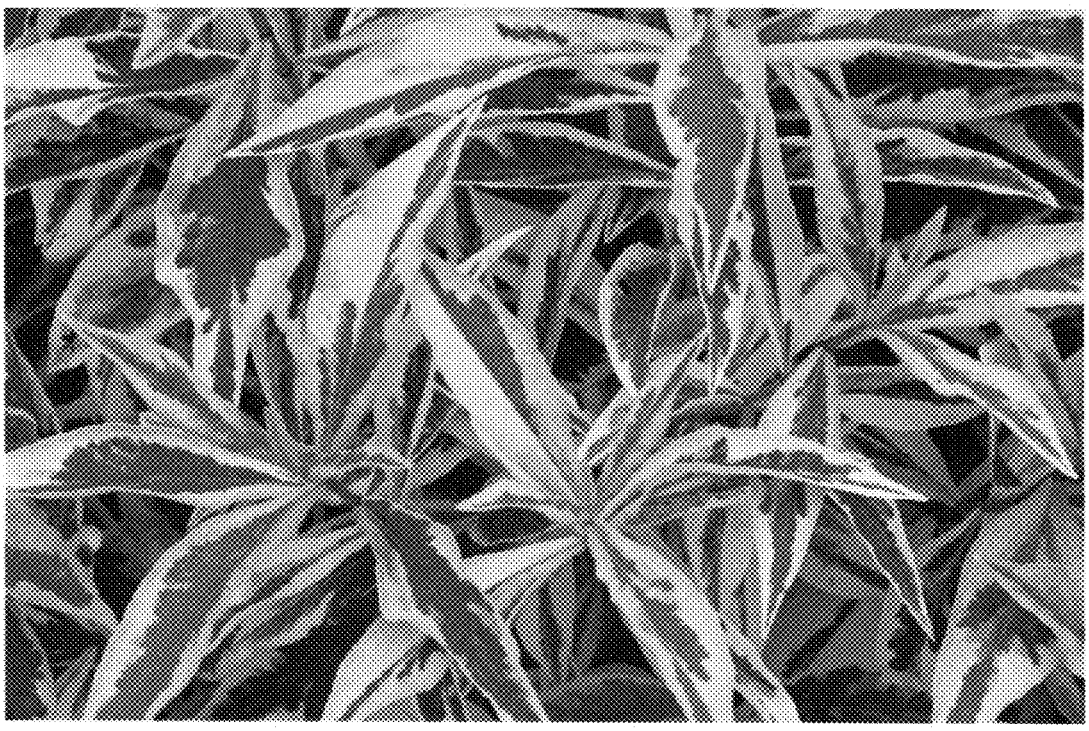
FIG. 1 shows the new plant with late spring to early summer foliage.
Figure 2:
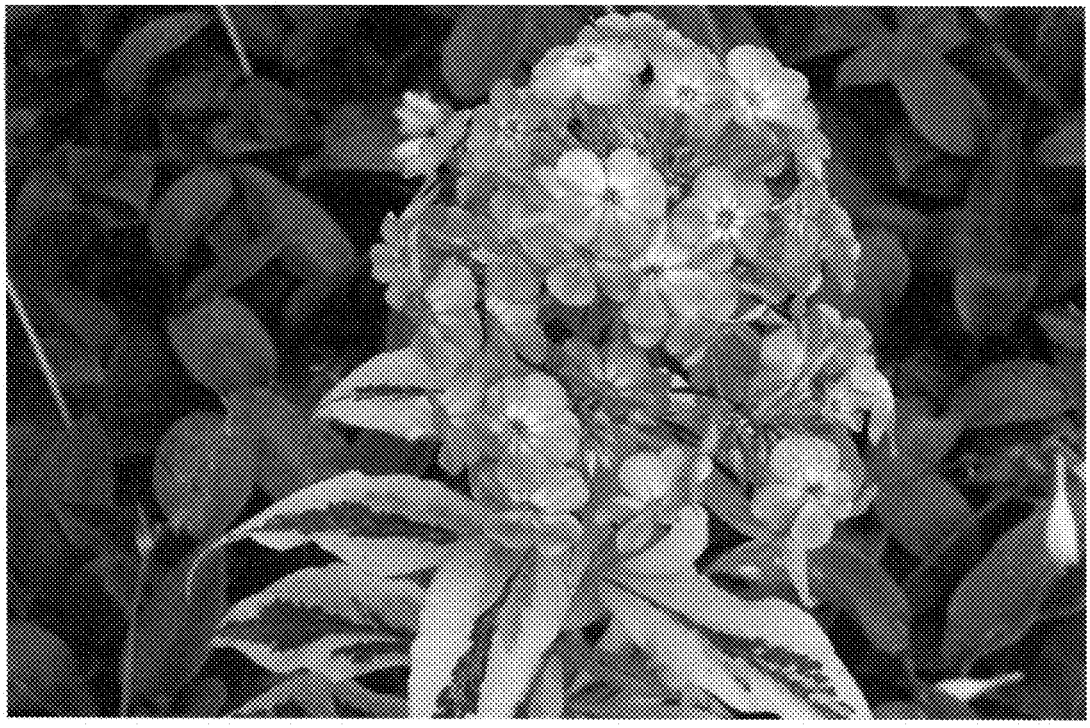
FIG. 2 shows the floriferous flower head of the new plant together with mid-summer foliage.

The following descriptions and color references are based on the 2001 edition of The Royal Horticultural Society Colour Chart except where common dictionary terms are used. *Phlox paniculata* 'Shockwave' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Phlox paniculata.*

Parentage: Non-induced whole plant mutation of *Phlox paniculata* 'David's Lavender'.

Plant habit: Hardy herbaceous perennial, compact, producing several rigid, basally-branched, upright stems; 30 to 45 cm tall at flowering and 18 to 24 cm wide; large rounded panicle cluster to 14.0 cm across and 15.0 cm tall; flowering begins late-summer in Michigan and continuing for about 4 weeks.

Propagation: Stem cuttings; rooting in about 14 days.

Time to produce finished crop in 3.8 liter pots: About 8 to 10 weeks; moderate rate of growth.

Root: Primary roots to about 3.0 mm thick; secondary fibrous and freely branching; color cream white to tan depending on soil type.

Leave: Simple, opposite, oblanceolate, entire, glabrous above and minutely pubescent below; acute apex, attenuate sessile base; 9.0 to 10.0 cm long by 2.5 to 3.0 cm wide in the center; variegated leaf margin variable between 2.0 mm and 11.0 mm wide.

Leaf color young foliage: Adaxial surface more gray than RHS 141A and more green than RHS 137A in the center; adaxial surface between RHS N144A and RHS N144C on the margin with variable intermediate sectors of nearest RHS N144D or more green than RHS 151D; abaxial surface between RHS 143A and RHS 144A in the center; abaxial surface same as adaxial side on the margin with variable intermediate sectors more green than RHS 145D and more yellow than RHS 146D.

Leaf color mid-season: Adaxial surface nearest RHS 136A in the center; adaxial surface nearest RHS 160D on the margin with intermediate sectors of lighter than RHS 147D; abaxial surface nearest N138A in the center and nearest RHS 160D on the margin with intermediate sectors of nearest RHS 141B.

Foliage fragrance: None detected.

Veins: Pinnate; minutely pubescent below and glabrous above; mid-vein about 1.0 mm wide at base, slightly sunken above and raised below.

Vein color: Nearest RHS 148C on the adaxial surface and nearest RHS 147C on abaxial surface.

Petiole: Leaves sessile.

Buds one to two days prior to opening: Petals twisted about each other, narrowly oblanceolate, acute apex with petals twisted about each other; about 1.0 cm long and 3.0 mm diameter.

Bud color: Nearest RHS 84D with slightly darker petal margins.

Flowers: Salverform, with fused tube about 2.4 cm long and limb about 2.6 cm across consisting of five petals; held in a branched panicle of about 90 flowers.

Flower longevity: About 5 days on plant or as cut flower; self-cleaning.

Flower fragrance: Pleasantly sweet.

Petals: Five, glabrous except for inner 5 mm of tube throat, rounded limbs with rounded to emarginate apex; limbs diameter about 1.5 cm, overlapping about 30%; base fused into a tube about 3.0 mm diameter and 2.4 cm long; surfaces with fine hairs the same color as petals.

Petal color:

*Adaxial surface of limb.*—Central eye of about 4.0 mm diameter nearest N66D, center bulls-eye extending to about 3.5 mm from center and outside of center eye of nearest lighter than RHS 75D, and outside of petal between RHS 75A and RHS 70C.

*Abaxial surface of limb.*—Between RHS 75C and RHS 75D.

*Adaxial surface of tube.*—Between RHS 75C and RHS 75D.

*Abaxial surface of tube.*—Lighter than RHS N74D.

Androecium:

*Filaments.*—Usually five, fused to inner petals, of varying lengths between 1.0 mm and 20 mm and less than 0.5 mm in diameter; lighter than RHS 69D.

*Anther.*—Oblong elliptic, about 3.0 mm by 1.0 mm wide, nearest RHS 158D.

*Pollen.*—Not yet observed.

Gynoecium:

*Pistil.*—One per flower.

*Style.*—Cylindrical; about 2.5 cm long and 0.5 mm diameter when flower is mature; lighter than RHS 69D at distal range and near white at base.

*Stigma.*—Split in the proximal 2 mm and about 0.25 mm in diameter; persistent after flower abscission; nearest; RHS 158D.

*Ovary.*—Inferior; elliptic, about 2.0 mm long and 1.0 mm diameter; between RHS 139D and RHS 138D.

Sepals: Five, glabrous or minutely and sparsely pubescent; lanceolate, with fused base and acute apex; about 7.0 mm long and 1.0 mm wide.

Sepal color: Nearest RHS 137B on both adaxial and abaxial surfaces.

Peduncle: Glaucous, stiff, strong, erect, rounded to about 0.5 cm across and 30.0 cm long; about 10 per plant; branched at distal nodes; about 30 to 35 nodes per peduncle; average internode length about 1.0 cm; peduncle color between RHS 138B and RHS 139C with nodes same color.

Fruit: Fruit and seed have not yet been observed.

Hardiness and culture: The new plant grows best with plenty of moisture and adequate drainage; hardy to at least from USDA zone 4 through 8.

Disease and pest resistance: *Phlox* 'Shockwave' demonstrated the same excellent powdery mildew resistance of the parent sport 'David's Lavender' under conditions that would show symptoms among all but the most resistant varieties.

I claim:

1. A new and distinct cultivar of Tall Garden *Phlox, Phlox paniculata* 'Shockwave', as herein described and illustrated, especially suitable as a potted plant, for the garden, for attracting hummingbirds and butterflies, and for cut flower arrangements.

* * * * *